United States Patent [19]  
Vali et al.

[11] 4,122,342  
[45] Oct. 24, 1978

[54] X-RAY AND GAMMA RAY WAVEGUIDE, CAVITY AND METHOD

[75] Inventors: Victor Vali, Salt Lake City, Utah; Reuben S. Krogstad; H. Robert Willard, both of Seattle, Wash.

[73] Assignee: University of Utah Research Institute, Salt Lake City, Utah

[21] Appl. No.: 787,172

[22] Filed: Apr. 13, 1977

[51] Int. Cl.² .............................................. G03B 41/16
[52] U.S. Cl. .................................. 250/272; 250/273; 250/505
[58] Field of Search ........................ 250/505, 272, 273

[56] References Cited

U.S. PATENT DOCUMENTS

| | | | |
|---|---|---|---|
| 2,559,972 | 7/1951 | Kirkpatrick | 250/505 |
| 3,143,651 | 8/1964 | Giacconi | 250/505 |
| 3,821,556 | 6/1974 | Hoover | 250/505 |

Primary Examiner—Craig E. Church

[57] ABSTRACT

An X-ray and Gamma ray waveguide, cavity, and method for directing electromagnetic radiation of the X-ray, Gamma ray, and extreme ultraviolet wavelengths. A hollow fiber is used as the waveguide and is manufactured from a material having an index of refraction less than unity for these wavelengths. The internal diameter of the hollow fiber waveguide and the radius of curvature for the waveguide are selectively predetermined in light of the wavelength of the transmitted radiation to minimize losses. The electromagnetic radiation is obtained from any suitable source and upon introduction into the waveguide is transmitted along a curvilinear path. The waveguide may be formed as a closed loop to create a cavity or may be used to direct the electromagnetic radiation to a utilization site.

11 Claims, 4 Drawing Figures

X-RAY AND GAMMA RAY WAVEGUIDE, CAVITY AND METHOD

BACKGROUND

1. Field of the Invention

This invention relates to fiber waveguides and, more particularly, to hollow fiber waveguides useful in transmitting electromagnetic radiation in the X-ray, Gamma ray, and extreme ultraviolet wavelengths.

2. The Prior Art

The shorter wavelength electromagnetic radiation in the X-ray, Gamma ray, and extreme ultraviolet wavelengths finds many applications in the industrial, scientific research, and medical fields. For example, it is a useful tool in various diagnostic, testing, treatment, and experimental procedures. However, by its inherent characteristics relating to its relatively short wavelengths, this type of electromagnetic radiation readily penetrates most materials and is somewhat difficult to direct or otherwise control. Control is of particular importance since usefulness of the radiation is frequently not considered by reason of extraneous events which otherwise mar the useful events.

This type of electromagnetic radiation has long been considered to be valuable in treating abnormal tissue growth in mammals. However, unless properly controlled and directed, hard or the very short wavelength X-ray and Gamma ray radiation has been known to cause significant damage to adjacent, healthy tissue as a resultant, unacceptable risk factor. For example, many abnormal tissue growths occur at a relatively deep internal location thereby requiring penetration of the overlying healthy tissue by the electromagnetic radiation in order to reach the abnormal tissue growth. The resultant radiation injury to healthy tissue is referred to in the art as "radiation sickness" and is frequently considered to be an undesirable but tolerated side effect for various types of radiation therapy.

The relatively longer wavelength X-ray, Gamma ray, and extreme ultraviolet wavelengths of electromagnetic radiation are generally classified as "soft X-rays" and are also useful in various applications. However, their ability to penetrate matter to significant depths is limited in addition to being difficult to direct or otherwise control as are the "hard X-rays". Since the subject electromagnetic radiation from the longer wavelentgh, extreme ultraviolet electromagnetic radiation to the shorter wavelength, "hard" X-ray and Gamma ray electromagnetic radiation are generally classed as X-ray and Gamma ray electromagnetic radiation, this latter terminology will be used throughout for ease of presentation and understanding of this invention.

Numerous industrial applications could also benefit from the transmittance of the subject electromagnetic radiation from a suitable source to a utilization site. For example, various nondestruct test procedures could be conducted by carefully directing the electromagnetic radiation only to the desired location while substantially minimizing irradiation of nonessential elements.

Advantageously, suitable means for confining or otherwise controlling the directional travel of electromagnetic radiation of the X-ray and Gamma wavelengths could also be incorporated into some form of laser apparatus. This would benefit from being able to develop a cavity for these wavelengths. The development of an X-ray and Gamma ray laser assumes that the gain of the medium is larger than the absorption losses in the cavity. Since the absorption losses are related, in part, to the loss features of the laser cavity, a low loss waveguide is useful as a laser cavity.

Accordingly, it would be a significant advancement in the art to provide a waveguide and method for suitably transmitting electromagnetic radiation of the X-ray and Gamma ray wavelength ranges. An even further advancement in the art would be to provide a method for transmitting electromagnetic radiation of the X-ray and Gamma ray wavelengths.

Numerous industrial applications could also benefit from the transmittance of the subject electromagnetic radiation from a suitable source to a utilization site. For example, various nondestruct test procedures could be made conducted by carefully directing the electromagnetic radiation only to the desired location while substantially minimizing irradiation of nonessential elements.

Advantageously, suitable means for confining or otherwise controlling the directional travel of electromagnetic radiation of the X-ray and Gamma wavelengths could also be incorporated into some form of laser apparatus. This would benefit from being able to develop a cavity for these wavelengths. The development of an X-ray and Gamma ray laser assumes that the gain of the medium is larger than the absorption losses in the cavity. Since the absorption losses are related, in part, to the loss features of the laser cavity, a low loss waveguide is useful as a laser cavity.

Accordingly, it would be a significant advancement in the art to provide a waveguide and method for suitably transmitting electromagnetic radiation of the X-ray and Gamma ray wavelengths from a source to a desired location. An even still further advancement in the art would be to provide a waveguide for X-ray and Gamma ray radiation wherein the waveguide is formed into a closed loop to create a cavity for the X-ray and Gamma ray radiation. Such an invention is disclosed and claimed herein.

BRIEF SUMMARY AND OBJECTS OF THE INVENTION

This invention relates to a waveguide and cavity apparatus and method for transmitting electromagnetic radiation of the X-ray and Gamma ray wavelength ranges. The waveguide is formed as a hollow fiber waveguide with the material of construction adjacent the hollow core of the waveguide having an index of refraction less than unity for the wavelengths of the electromagnetic radiation of interest. Importantly, the waveguide may be bent along a curvilinear path and even formed into a closed loop to create a cavity for laser-type operation at the subject wavelengths. Care is taken to insure that the radius of curvature for the waveguide does not exceed certain predeterminable limits to thereby decrease bending losses in the waveguide.

It is, therefore, a primary object of this invention to provide improvements in the method for transmitting electromagnetic radiation of the X-ray and Gamma ray wavelength ranges.

Another object of this invention is to provide a waveguide useful for transmitting electromagnetic radiation of the X-ray and Gamma ray wavelength ranges.

Another object of this invention is to provide improvements in the art of transmitting electromagnetic radiation of the X-ray and Gamma ray wavelengths from a radiation source to a remote location.

Another object of this invention is to provide a cavity for electromagnetic radiation of the X-ray and Gamma ray wavelengths.

These and other objects and features of the present invention will become more fully apparent from the following description and appended claims taken in conjunction with the accompanying drawing.

DETAILED DESCRIPTION OF THE PREFERRED EMBODIMENTS

General Discussion

Figure 4:
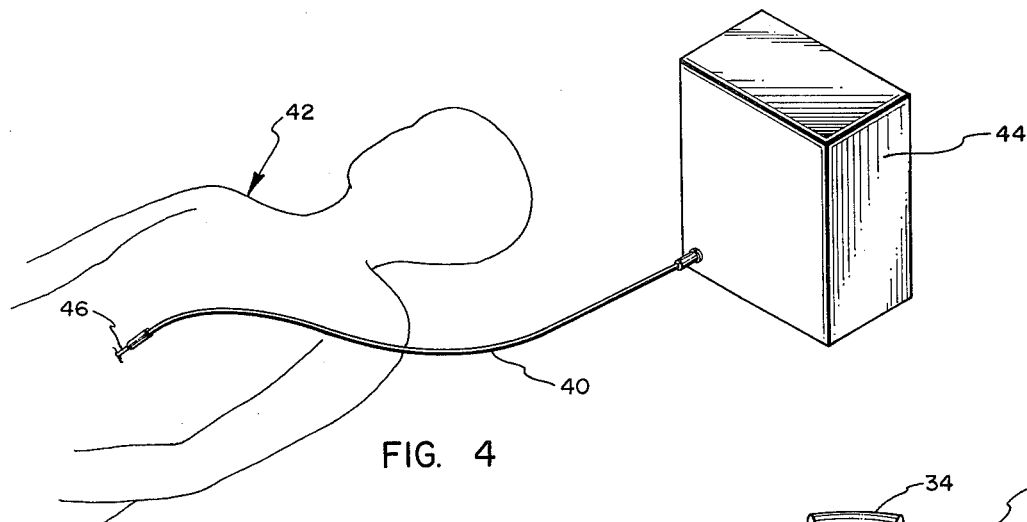
FIG. 4 is a schematic perspective view of one preferred embodiment of the invention in an environment of use.

Electromagnetic radiation of the X-ray and Gamma ray wavelength ranges has been known since about 1919 to have for various materials an index of refraction less than unity (1). Unity is the value of index of refraction of vacuum. Accordingly, there is an angle of total reflection when such electromagnetic radiation is directed at a surface at a sufficiently low angle of incidence. Representative angles of total reflection for various materials at different wavelengths are listed in table I, below:

TABLE I

| Material | Critical Angle of Total Reflection | |
|---|---|---|
| | Wave Length (Angstroms) | Critical Angle |
| Glass | 0.7078 | 6'10" |
| Calcite | 1.537 | 14'25" |
| Calcite | 3.734 | 34'25" |
| Quartz | 10.0 | 91'40" |
| Nickel | 0.7078 | 10'15" |
| Nickel | 1.389 | 16'9" |
| Nickel | 1.537 | 24'40" |
| Silver | 0.7078 | 11'42" |
| Silver | 1.537 | 26'42" |
| Copper | 1.389 | 19'36" |
| Copper | 1.537 | 20'24" |
| Gold | 1.537 | 31'24" |

(see Introduction to Modern Physics, Richtmyer and Kennard, McGraw Hill (1947) pp. 525, 526)

The foregoing data presented in Table I indicates that if the angle of incidence is small enough, there will be total reflection of the incident radiation. This angle is designated by the Greek letter theta, $\theta_R$, and is a function of the wavelength of the incident radiation as well as the material forming the reflective surface. Accordingly, following the law of optics, total reflection should occur for glancing angles less than $\theta_R$. This information is useful for constructing a cavity for producing Gamma ray amplification by stimulated emission of radiation. This phenomena is analogous to the maser and laser phenomena and could, therefore, be referred to as a gaser.

The condition for superradiance of any system containing inverted population atoms is that the gain of the medium has to be larger than the absorption losses. The resultant gain $g$ is $g = g = e^{N\sigma x} - kx$ where N is the number density of inverted population atoms, $\sigma$ is the induced emission cross section, $K$ is the absorption coefficient and $x$ is the distance traveled by the radiation in the medium.

Therefore the condition for superradiance is $$\sigma N > k \text{ or } N > k/\sigma \tag{1}$$

This means that there is a minimum required inverted population density N below which superradiance or induced emission is not possible. For X-rays the mass absorption coefficients $k/\rho$ are tabulated. The induced emission cross section $\sigma$ is given by:

$$\sigma = 2\pi \lambdabar^2 \frac{\gamma_i}{\gamma_i + \gamma_f} \frac{2J_f + 1}{2J_i + 1} \tag{2}$$

where $\lambdabar = \lambda/2\pi$ is the wavelength of the radiation, $\delta_i$ and $\delta_f$ are the reciprocal lifetimes of the initial and final states, respectively, and $J_i$ and $J_f$ are the angular quantum numbers of the initial and final states. For $K\alpha_1$ X-ray line $\delta_f = O$, $J_i = 3/2$ and $J_f = 1/2$ hence:

$$\sigma = \pi \lambdabar^2 \tag{3}$$

and the condition for superradiance is $$N > \frac{K}{\pi \lambdabar^2} \tag{4}$$

For example for aluminum and copper the numerical values of the relevant quantities are for $K\alpha_1$ line:

| | Al | Cu |
|---|---|---|
| $\lambda$ | 9Å | 1.5 Å |
| $\sigma$ | $6 \cdot 10^{-16}$ cm$^2$ | $1.8 \cdot 10^{-17}$ cm$^2$ |
| $K/\rho$ | 300 | 50 |
| k | 800 | 450 |

Hence the required number density of $K\alpha$ excited atoms are $$N\text{al} > 1.3 \cdot 10^{18}$$

$$N\text{cu} > 2.5 \cdot 10^{19} \tag{6}$$

This is to be compared with the number densities of atoms in metallic aluminum and copper:

$$N\text{al} = 6 \cdot 10^{22}$$

$$N\text{cu} = 8 \cdot 10^{22} \tag{7}$$

Thus about $2 \cdot 10^{-5}$ of the aluminum atoms and $3 \cdot 10^4$ of the copper atoms have to be excited.

The efficiency of producing inverted populations of X-ray levels is under normal X-ray tube conditions (approximately 5 times the voltage required to remove a shell electron) about 1%. For example, for copper more than 50% of the X-rays emitted are in form of $K\alpha$ lines. The $K\alpha_1$ line usually contains more than half of the energy in X-ray line spectrum. Thus conservative estimates indicate that at least $2 \cdot 10^{-3}$ of the energy contained in the primary electron beam is converted into useful inverted population energy.

This can be obtained with presently available flash X-ray tubes (using Van de Graaf generators with Bennett electrodes). It is also believed that a required nuclear inverted population density can be obtained at present.

Figure 1:
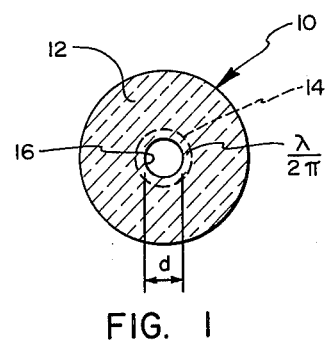
FIG. 1 is an enlarged, transverse cross section of the waveguide.

With particular reference to FIG. 1, the attenuation of a hollow fiber waveguide can be estimated from the cross sectional area of the hollow fiber core and the effective area of the evanescent radiation penetration into the surrounding structure, $\lambda/2\pi$. For example, a hollow fiber waveguide is shown at 10 in cross section. The structure or cladding is indicated at 12 with the evanescent radiation penetration into cladding 12 shown by broken lines 14 and indicated by $\lambda/2\pi$. The letter $d$ indicates the diameter of the hollow core 16 of the fiber 10. For purposes of this illustration, if we assume that the diameter $d$ of core 16 is $d = 1$ micrometer, then the cross sectional area A of core 16 is:

$$A = \frac{\pi d^2}{4} = \frac{\pi \cdot 10^{-8}}{4} \text{ cm}^2 \tag{8}$$

For a wavelength, $\lambda$, of electromagnetic radiation inside core 16 wherein $\lambda = 1\text{Å}$ ($\text{Å}$ = Angstrom unit), the effective penetration area is $$\frac{\pi d \lambda}{2\pi} = \frac{d\lambda}{2} \tag{9}$$

Therefore, the ratio is:

$$\frac{d\lambda}{2} \cdot \frac{4}{\pi d^2} = \frac{\lambda}{\pi d} = \frac{2 \cdot 10^{-8}}{\pi \cdot 10^{-4}} \simeq 6 \cdot 10^{-5} \tag{10}$$

and the attenuation is diminished by $6 \cdot 10^{-5}$ as compared with solid glass. Such a waveguide can be curved to form a complete loop and, accordingly, accommodates formation of a resonant cavity for the X-rays and Gamma rays.

Figure 2:
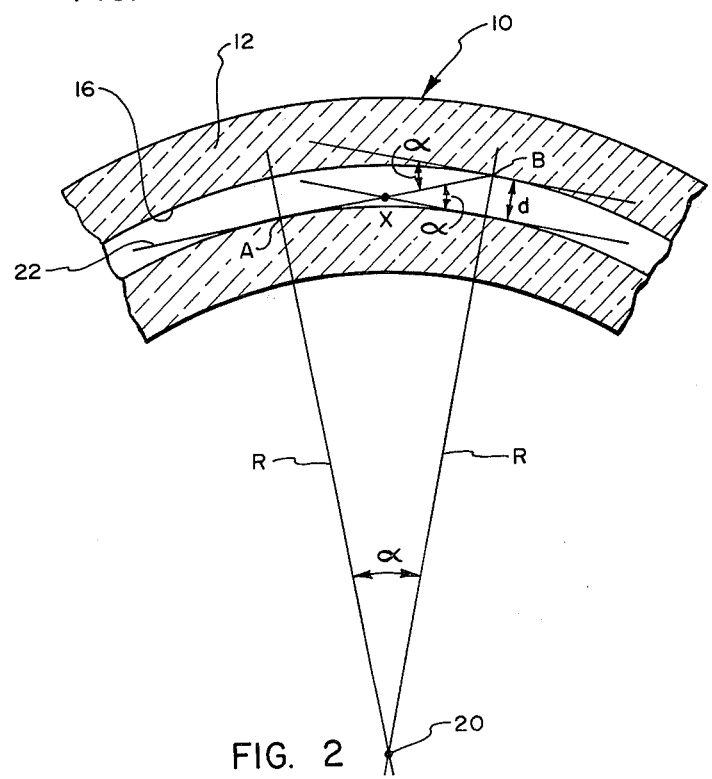
FIG. 2 is an enlarged, longitudinal cross section of the waveguide.

Referring more particularly to FIG. 2, the waveguide 10 is shown in a longitudinal cross section with cladding 12 and core 16 bent along an arc having its center at 20 and a radius of curvature R. The geometry of the angles of reflection for core 16 is illustrated achematically by a beam of radiation 22 tangentially touching the wall of core 16 at point A and striking the opposite wall of core 16 at point B and at an angle $\alpha$. The angle $\alpha$ must be equal to or less than the angle of total reflectance, $\theta_R$, as set forth hereinbefore to assure propogation of beam 22 through core 16.

The angle $$\alpha = \frac{X}{R} \text{ or } \frac{d2}{X} \text{ or } x = \frac{2d}{\alpha}.$$
$$\text{If } \alpha = \frac{2d}{R\alpha}, R = \frac{2d}{\alpha^2}.$$

Accordingly, if $\alpha = 0.5° \simeq 10^{-2}$ radians and $d = 10^{-4}$ cm., then the minimum radius of curvature is $$R = \frac{2 \cdot 10^{-4}}{10^{-4}} = 2 \text{ cm.}$$

Furthermore, where $\alpha = 0.1° = 2 \cdot 10^{-3}$ radians ($d = 10^{-4}$ cm.), the minimum allowed radius of curvature R is:

$$R = \frac{2 \cdot 10^{-4}}{(2 \cdot 10^{-3})^2} = 0.5 \cdot 10^{-2} \text{cm} = 50 \text{ cm} \tag{11}$$

Figure 3:
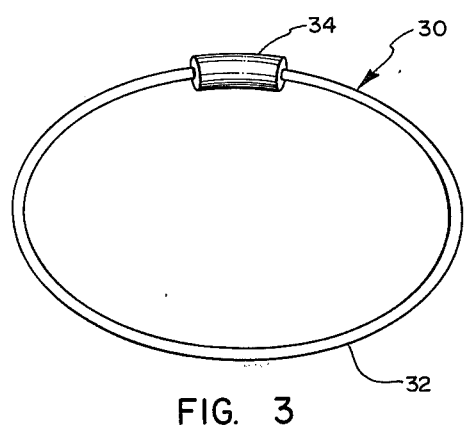
FIG. 3 is a plan view of the waveguide of this invention formed into a closed loop so as to create a cavity.

The Illustrated Embodiment of FIG. 3

Referring now more particularly to FIG. 3, a cavity is shown generally at 30 and is formed from a closed loop of fiber waveguide 32 and is similar to waveguide 10 (FIGS. 1 and 2). Importantly, the radius of curvature of the waveguide 32 forming cavity 30 is specifically configurated so as to not exceed the curvature limitations discussed with respect to FIG. 2, above. As such, there is essentially good transmittance of the electromagnetic radiation of the X-ray and Gamma ray wavelengths around cavity 30 in a manner analogous to a laser cavity. Accordingly, it is now possible to develop X-ray and Gamma ray amplification by stimulated emission of radiation since the cavity provides a continuous path. To this end, the inclusion of a suitable gain medium 34 is considered desirable so as to provide the necessary electromagnetic radiation source of the X-ray and Gamma ray wavelength range.

The Illustrated Embodiment of FIG. 4

Referring now more particularly to FIG. 4, one preferred embodiment of a useful application of this invention is illustrated schematically. In particular, a useful medical application is shown in treatment of a patient 42. The treatment apparatus includes a waveguide 40 of this invention suitable for transmitting electromagnetic radiation of the X-ray and Gamma ray wavelengths and a source 44 for this electromagnetic radiation. Source 44 can be any suitable source for the electromagnetic radiation transmitted by waveguide 40 and may include, by way of example, an X-ray source or a radioactive material as the Gamma ray source.

Advantageously, source 44 should be suitably adjustable with respect to frequency and intensity so as to enable the operator (not shown) to adjust the electromagnetic radiation transmitted through waveguide 40. Additionally, waveguide 40 is shown as having a probe 46 formed on the end thereof. Probe 46 is configurated as a suitable hollow, needle-like apparatus to accommodate penetration of the flesh of patient 42 to place the end thereof (hidden) in the desired proximity to an abnormal tissue growth (not shown) in patient 42. Treatment is commenced by suitably directing the predetermined electromagnetic radiation from source 44 through waveguide 40 and probe 46 into patient 42.

Importantly and surprisingly, waveguide 40 enables the operator (not shown) to preselect the desired frequencies and radiation dosages for the electromagnetic radiation from source 44 and introduce the same into patient 42 through the curvilinear path of waveguide 40 without unwanted damage or exposure of areas not intended to be exposed. For example, the treatment can be accomplished with "soft" X-rays at the tissue site whereas such "soft" x-rays would not be of such a nature as to sufficiently penetrate the enclosing healthy tissue. Additionally, the "soft" X-rays do not penetrate appreciably beyond the tissue undergoing treatment so that the operator is able to very precisely irradiate only the tissue to be treated. This represents a substantial improvement over the recent development toward the treatment of malignant tissue in the breast whereby an interstitial implant of iridium 192 is used as the radiation source. In particular, the precision with which the wavelength, dosage and placement may be determined provides a surprisingly improved treatment procedure.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All Changes which come within the meaning and range of equivalency of the claims are to be embraced within their scope.

What is claimed and desired to be secured by United States Letters Patent is:

1. A waveguide for electromagnetic radiation of the X-ray and Gamma ray wavelength ranges comprising a waveguide having a hollow core, the material of construction adjacent the hollow core having an index of refraction less than unity for said electromagnetic radiation.

2. The waveguide defined in claim 1 wherein the hollow core is evacuated.

3. The waveguide defined in claim 1 wherein the waveguide is bent along a curvilinear path wherein the radius of curvature is defined by the formula $R = 2d/\alpha^2$ wherein $R$ is the radius of curvature, $d$ is the diameter of the hollow core of the waveguide and $\alpha$ is the angle of total reflection of the waveguide material as determined by the wavelength of the electromagnetic radiation and the waveguide material.

4. The waveguide defined in claim 3 wherein the waveguide is formed into a closed curvilinear path to thereby provide a cavity.

5. A method for conducting electromagnetic radiation having a wavelength in the X-ray and Gamma ray wavelength range from a source to a second position comprising the steps of:

obtaining a waveguide for the electromagnetic radiation, the waveguide comprising a hollow fiber with the material of the fiber adjacent the hollow having an index of refraction less than unity, the waveguide having a first end and a second end;

directing the electromagnetic radiation from the source axially into the first end of the hollow waveguide; and placing the second end of the waveguide in the second position thereby directing the electromagnetic radiation from the source to the second position through the hollow waveguide.

6. The method defined in claim 5 wherein the placing step comprises orienting the waveguide along a curvilinear path.

7. The method defined in claim 6 wherein the orienting step comprises limiting the arc of curvature of the waveguide to a radius of curvature defined by the formula:

$$R = 2d/\alpha^2$$

wherein R is the radius of curvature, $d$ is the diameter of the hollow core of the waveguide and $\alpha$ is the angle of total reflection as determined by the wavelength of the electromagnetic radiation and the material of the waveguide adjacent the hollow core.

8. The method defined in claim 5 wherein the placing step further comprises forming a complete loop with the waveguide thereby creating a cavity for the amplification of the electromagnetic radiation by stimulated emission of radiation, the forming step comprising limiting the radius, R, of the arc of curvature of the complete loop to a value greater than $R = 2d/\alpha^2$ wherein $d$ is the diameter of the hollow core of the waveguide and $\alpha$ is the angle of total reflection as determined by the wavelength of the electromagnetic radiation and the material of the waveguide adjacent the hollow core.

9. The method defined in claim 5 wherein the placing step further comprises inserting the second end into an object to be irradiated by the electromagnetic radiation and preselecting the wavelength of the electromagnetic radiation according to the material and mass of the object to be irradiated.

10. The method defined in claim 9 wherein the inserting step comprises enclosing a portion of the second end in a hollow needle and piercing a body with the needle to place the second end adjacent tissue to be irradiated by the electromagnetic radiation.

11. An apparatus for the amplification of electromagnetic radiation of the X-ray and Gamma ray wavelength by stimulated emission of radiation comprising:

a cavity comprising a waveguide formed into a closed loop; and a gain medium electromagnetically coupled to the cavity, the gain medium operable to emit electromagnetic radiation of the X-ray and Gamma ray wavelength.

* * * * *